United States Patent [19]

Costantini et al.

[11] 4,208,339

[45] Jun. 17, 1980

[54] PROCESS FOR THE PREPARATION OF PARA-BENZOQUINONE

[75] Inventors: Michel Costantini, Lyon; Michel Jouffret, Francheville Le Bas, both of France

[73] Assignee: Rhone-Poulenc Industries, Paris, France

[21] Appl. No.: 918,579

[22] Filed: Jun. 23, 1978

[30] Foreign Application Priority Data

Jun. 27, 1977 [FR] France ................................ 77 20709

[51] Int. Cl.$^2$ ...................... C07C 45/16; C07C 49/64
[52] U.S. Cl. ................................. 260/396 R; 568/772
[58] Field of Search .................................... 260/396 R

[56] References Cited

U.S. PATENT DOCUMENTS

| | | | |
|---|---|---|---|
| 3,549,670 | 12/1970 | Spousta | 260/396 N |
| 3,870,731 | 3/1975 | Hutchings | 260/396 R |
| 3,935,247 | 1/1976 | Kothari | 260/396 R |

*Primary Examiner*—Vivian Garner
*Attorney, Agent, or Firm*—Burns, Doane, Swecker & Mathis

[57] ABSTRACT p-Benzoquinone is prepared by oxidizing phenol with molecular oxygen or with a gas in which oxygen is present, in the liquid phase, in the presence of cuprous or cupric ions. The improvement resides in carrying out the reaction in the presence of a metal, in the metallic form, which is selected from the group consisting of nickel, iron, tin, cobalt, chromium, molybdenum, magnesium and copper. The resultant p-benzoquinone is useful as an industrial source of hydroquinone, which is employed in photography.

19 Claims, No Drawings

PROCESS FOR THE PREPARATION OF PARA-BENZOQUINONE

BACKGROUND OF THE INVENTION

1. Field of the Invention

The present invention relates to a process for the preparation of para-benzoquinone by oxidizing phenol with oxygen or with a gas in which oxygen is present.

2. Discussion of the Prior Art

Para-benzoquinone, which will hereinafter be denoted more simply, as "benzoquinone" or "p-benzoquinone", is an organic product of particular importance industrially because it affords, by hydrogenation, hydroquinone. The latter compound is widely used in the photographic industry.

3. Description of the Prior Art

Numerous processes for the preparation of hydroquinone from phenol have been previously proposed; these processes essentially involve the hydroxylation of phenol with hydrogen peroxide itself or with organic peracids such as peracetic and performic acids which are generated in situ from hydrogen peroxide and the carboxylic acid. In all cases, these processes lead to the concomitant formation of hydroquinone and pyrocatechol, the latter product generally being formed in preponderant amounts. Certain of these processes of hydroxylation with hydrogen peroxide have shown themselves to be of great value and are the subject of industrial exploitation for the production of diphenols. Nevertheless, industry is seeking a process which makes it possible to obtain hydroquinone from phenol selectively, while limiting or even totally avoiding the formation of the other diphenols and especially of pyrocatechol. A means of resolving this problem would be the perfection of a process for the selective oxidation of phenol to benzoquinone with molecular oxygen or with a gas in which oxygen is present.

Thus, the French patent application published under No. 2,245,602 describes a process for the preparation of benzoquinones from various phenols, and especially of benzoquinone from phenol, by oxidation with molecular oxygen or with a gas in which oxygen is present (for example, air), in the presence of a catalyst comprising copper and a chloride, bromide, iodide, thiocyanate, cyanate or cyanide ligand, in a polar solvent. Although copper metal can be employed under conditions which enable it to be oxidized to cuprous or cupric ions, it is generally copper salts, especially cuprous or cupric halides and, in particular, cupric chloride, which are used. U.S. Pat. No. 3,987,068 has proposed an analogous process by which the reaction is carried out in the presence of a copper salt in a nitrile which forms a complex with the copper salt. Although these processes generally ensure a good degree of conversion of the phenol and industrially valuable yields of benzoquinone, it has been found that when the process is carried out in a reaction apparatus which is not inert towards the reaction medium—i.e., an apparatus made of steel or iron—its walls are rapidly attacked to such an extent that it is virtually impossible to envisage the use of such a process in industry. On the other hand, it has been found that, if equipment is used which is inert towards the reaction medium, such as, for example, reactors made of enamelled metal or of tantalum, no oxidation of the phenol occurs when the reaction is carried out in the presence of copper-II ions.

SUMMARY OF THE INVENTION

The present invention provides, in a process for the preparation of para-benzoquinone by oxidizing phenol with molecular oxygen or with a gas in which oxygen is present, in the liquid phase, in the presence of cuprous or cupric ions, the improvement comprising contacting the reactants in the presence of a metal, in the metallic form, which is selected from the group consisting of nickel, iron, tin, cobalt, chromium, molybdenum, magnesium and copper.

DETAILED DESCRIPTION OF THE INVENTION

The form in which the free metal is used in the process of the present invention is not critical. In general, the metal is employed in a divided form, for example as granules, powder or shavings.

The reaction is generally carried out in a polar solvent. Suitable solvents include nitriles, lower aliphatic alcohols (i.e., alcohols having from 1 to 4 carbon atoms), amides derived from secondary amines, and sulphoxides. Especially preferred are solvents selected from the group consisting of acetonitrile, methanol, dimethylformamide and dimethylsulfoxide.

Various copper salts can be used as the source of copper-I or copper-II ions; however, copper halides (in particular cuprous or cupric chlorides) and cupric nitrate are preferably employed. It has been found that, when cuprous derivatives such as $Cu_2Cl_2$ are used as the catalyst, the presence of any one of the above-mentioned free metals makes it possible, all other things being equal, to obtain higher degrees of conversion of the phenol, which improves the productivity of the reaction.

The amount of copper catalyst, expressed as the number of copper ions per mol of phenol, can vary widely. In general, this amount represents from 0.01 to 5 copper ions per mol of phenol; however, from a practical point of view, it is not desirable to employ amounts of catalyst which introduce more than 1 copper ion per mol of phenol. Thus, from 0.02 to 1 copper ion is generally used per mol of phenol.

The amount of metal used together with the copper is generally between 0.1 and 10 gram-atoms per copper ion present, and preferably between 0.1 and 1 gram-atom per copper ion. Among these metals, nickel, iron and copper are preferably employed.

The temperature at which the reaction is carried out can vary within wide limits. Temperatures from 10° to 120° C., and preferably from 20° to 100° C., are very suitable. The oxidation is carried out under a partial pressure of oxygen of at least 5 bars. Although there is no critical upper pressure limit, partial pressures of oxygen of not more than 100 bars, and preferably of not more than 50 bars, are used in practice.

The gas containing molecular oxygen can be air or oxygen-deficient or oxygen-enriched air, or mixtures of oxygen with various inert gases.

The concentration of phenol in the solvent is not critical and can vary considerably.

It has also been found that the process according to the present invention can be carried out in the presence of alkali metal or alkaline earth metal halides in order to increase the reaction rate. The fluorides, chlorides and bromides of lithium, potassium and sodium are preferably employed. The amount of these salts is generally between 0.1 and 5, and preferably between 0.5 and 2, mols per copper ion.

From a practical point of view, the reaction is preferably carried out in pressure-resistant equipment which is inert towards the reaction mixture, such as autoclaves made of steel which has been enamelled or coated with tantalum.

The invention will appear more fully from the examples which follow. These examples are given by way of illustration only and are not to be construed as limiting the invention either in spirit or in scope as many modifications both in materials and methods will be apparent to those skilled in the art.

EXAMPLE 1

90 cm$^3$ of methanol, 0.0755 mol of phenol, 0.022 mol of CuCl$_2$ and 0.022 gram-atom of nickel in powder form were successively introduced into an 0.5 liter tantalum-coated autoclave which was agitated by shaking. The autoclave was closed, air was introduced up to a pressure of 100 bars and the contents of the autoclave were then heated at 65° C. for 2 hours, with stirring. After cooling, the reaction mixture was degassed and the remaining phenol, the p-benzoquinone and, if necessary, the diphenols therein, were determined by gas phase chromatography and polarography.

Under these conditions, the degree of conversion of the phenol was 64% and the yield of para-benzoquinone, relative to the phenol converted, was 68.5%.

By way of comparison, the preceding experiment was repeated, the reaction being carried out in the absence of nickel. After 2 hours, not even the slightest oxidation of phenol was observed.

EXAMPLE 2

The procedure of Example 1 was followed, 0.00755 gram-atom of nickel being introduced instead of 0.022. The degree of conversion of the phenol was 49.4% and the yield of p-benzoquinone was 59.5%.

EXAMPLE 3

The procedure of Example 1 was followed, 0.022 mol of lithium fluoride being added to the reaction medium. The degree of conversion of the phenol was 79.5% and the yield of p-benzoquinone was 39%.

EXAMPLE 4

The procedure of Example 1 was followed, the cupric chloride being replaced with 0.022 mol of cupric nitrate and the reaction being carried out in the presence of 0.044 mol of lithium chloride. The degree of conversion of the phenol was 83% and the yield of p-benzoquinone was 47.5%.

EXAMPLE 5

The procedure of Example 1 was followed, but the methanol was replaced with 24 cm$^3$ of acetonitrile and the nickel was replaced with 0.00475 gram-atom of copper metal. The amount of CuCl$_2$ introduced was 0.00475 mol. After 1 hour at 50° C. under an air pressure of 100 bars, the degree of conversion of the phenol was 78% and the yield of p-benzoquinone was 56%.

By way of comparison, this experiment was repeated, the reaction being carried out in the absence of copper metal. After 1 hour, the degree of conversion of the phenol was 9% and no p-benzoquinone had been formed.

EXAMPLE 6

90 cm$^3$ of acetonitrile, 0.0755 mol of phenol, 0.022 mol of CuCl$_2$ and 0.022 gram-atom of iron metal were introduced into the autoclave of Example 1. After 2 hours at 65° C. under an air pressure of 100 bars, the degree of conversion of the phenol was 100% and the yield of p-benzoquinone was 68%.

EXAMPLES 7 TO 10

The reaction was carried out under the conditions of Example 1, in the presence of various metals and of lithium chloride (0.044 mol). The results are recorded in the following table:

| EX-AMPLE | METAL NATURE | AMOUNT IN GRAM-ATOMS | DC (1) OF PHENOL % | Y (2) OF BENZO-QUINONE % |
|---|---|---|---|---|
| 7 | Ni | 0.022 | 98.5 | 54 |
| 8 | Co | 0.022 | 100 | 58 |
| 9 | Mg | 0.022 | 98.7 | 25 |
| 10 | Cr | 0.022 | 96.7 | 65 |

(1) degree of conversion
(2) yield relative to the phenol converted

EXAMPLES 11 AND 12

The reaction was carried out under the conditions of Example 6, the iron being replaced by tin and nickel. The degrees of conversion were 100% in both cases and the yields of benzoquinone were 49% and 63%, respectively.

EXAMPLES 13 AND 14

40 cm$^3$ of acetonitrile, 0.085 mol of phenol, 0.0056 mol of cuprous chloride and 0.0056 gram-atom of nickel were introduced into the autoclave described in Example 1. After 1 hour at 50° C. under an air pressure of 100 bars, the degree of conversion of the phenol was 67% and the yield of p-benzoquinone, relative to the phenol converted, was 52%.

All other things being equal, when the above reaction was carried out in the absence of nickel, the degree of conversion of the phenol was only 56.5% and the yield of p-benzoquinone was only 53.5%.

EXAMPLE 15

The procedure of Example 6 was followed, the acetonitrile being replaced by 90 cm$^3$ of dimethylformamide and the reaction being carried out at 70° C. The degree of conversion of the phenol was 63% and the yield of p-benzoquinone was 49%.

While the invention has now been described in terms of various preferred embodiments and illustrated with respect to certain examples, it will be apparent to the skilled artisan that various omissions, substitutions, modifications and the like may be made without departing from the spirit of the invention. Accordingly, it is intended that the scope of the present invention be limited only by the following claims.

What is claimed is:

1. In a process for the preparation of p-benzoquinone by oxidizing phenol with molecular oxygen or with a gas in which oxygen is present, in the liquid phase, in the presence of cuprous or cupric ions, the improvement comprising contacting the reactants in the presence of a metal, in the metallic form, selected from the group consisting of nickel, iron, tin, cobalt, chromium, molybdenum and magnesium.

2. The process according to claim 1, wherein the copper ions are in the form of cupric chloride, cuprous chloride or cupric nitrate.

3. The process according to claim 1 wherein the amount of copper ions per mol of phenol is from 0.01 to 5.

4. The process according to claim 3 wherein the amount of copper ions per mol of phenol is from 0.02 to 1.

5. The process according to claim 1 wherein the amount of free metal, expressed in gram-atoms of metal per copper ion, is from 0.1 to 10.

6. The process according to claim 5 wherein the amount of free metal, expressed in gram-atoms of metal per copper ion, is from 0.1 to 1.

7. The process according to claim 1 further comprising conducting the reaction in the presence of an alkali metal halide or alkaline earth metal halide.

8. The process according to claim 7 wherein the alkali metal halide is lithium chloride or lithium bromide.

9. The process according to claim 8 wherein the amount of lithium chloride or lithium bromide is from 0.1 to 5 mols per copper ion.

10. The process according to claim 9 wherein the amount of lithium chloride or lithium bromide is from 0.5 to 2 mols per copper ion.

11. The process according to claim 7 wherein the amount of alkali metal halide or alkaline earth metal halide is from 0.1 to 5 mols per copper ion.

12. The process according to claim 11 wherein the amount of alkali metal halide or alkaline earth metal halide is from 0.5 to 2 mols per copper ion.

13. The process according to claim 1 wherein the reaction is conducted in an inert polar solvent.

14. The process according to claim 13 wherein the inert polar solvent is selected from the group consisting of methanol, acetonitrile, dimethylformamide and dimethylsulfoxide.

15. The process according to claim 1 wherein the reaction is conducted at a temperature of from 10° to 120° C. and at a partial pressure of oxygen of from 5 to 100 bars.

16. The process according to claim 15 wherein the temperature is from 20° to 100° C.

17. The process according to claim 15 wherein the pressure is from 5 to 50 bars.

18. The process according to claim 1 wherein the reaction is conducted in equipment which is inert towards the reaction medium.

19. The process according to claim 1 wherein the gas in which oxygen is present is air.

* * * * *